(12) United States Patent
Sung et al.

(10) Patent No.: US 8,011,829 B2
(45) Date of Patent: Sep. 6, 2011

(54) COMPACT AND LIGHTWEIGHT X-RAY DEVICE

(75) Inventors: Ki-Bong Sung, Goyang-Si (KR); Jong-Lae Park, Seoul (KR)

(73) Assignee: Poskom Co., Ltd., Paju-si, Gyeonggi-Do (KR)

( * ) Notice: Subject to any disclaimer, the term of this patent is extended or adjusted under 35 U.S.C. 154(b) by 190 days.

(21) Appl. No.: 12/349,871

(22) Filed: Jan. 7, 2009

(65) Prior Publication Data

US 2009/0175413 A1    Jul. 9, 2009

(30) Foreign Application Priority Data

Jan. 8, 2008 (KR) .................. 10-2008-0002070

(51) Int. Cl.
  *G01D 18/00* (2006.01)
(52) U.S. Cl. ................. 378/207; 378/63; 378/153
(58) Field of Classification Search .......... 378/62, 378/63, 147–153, 166, 206, 207
  See application file for complete search history.

(56) References Cited

U.S. PATENT DOCUMENTS

| | | | |
|---|---|---|---|
| 4,502,147 A | 2/1985 | Michaels | |
| 4,521,905 A * | 6/1985 | Hosokawa | 378/206 |
| 4,603,427 A | 7/1986 | Alpern et al. | |
| 6,863,439 B2 * | 3/2005 | Morris | 378/192 |
| 7,020,245 B2 * | 3/2006 | Noguchi | 378/150 |
| 7,281,849 B2 * | 10/2007 | Sohal et al. | 378/206 |
| 2004/0258211 A1 | 12/2004 | Scheuering | |

FOREIGN PATENT DOCUMENTS

| | | |
|---|---|---|
| DE | 4003757 A1 | 8/1991 |
| EP | 0325158 A2 | 7/1989 |
| EP | 0564292 A2 | 10/1993 |
| JP | 7047063 A | 2/1995 |
| JP | 11244282 A | 9/1999 |
| WO | 2007060049 A1 | 5/2007 |

* cited by examiner

*Primary Examiner* — Jurie Yun
(74) *Attorney, Agent, or Firm* — Lowe Hauptman Ham & Berner LLP

(57) ABSTRACT

An X-ray device for irradiating a beam of X-rays on an object to capture an X-ray image of the object is smaller in size and weight than conventional ones. The X-ray device includes an X-ray tube for generating the beam of X-rays and irradiating the beam of X-rays on the object, a shutter arranged around an X-ray irradiation axis for regulating an X-ray irradiation region on which the beam of X-rays is irradiated through the object, and a visual indicator unit arranged on the shutter for movement together with the shutter, the visual indicator unit being designed to visually indicate the X-ray irradiation region. In the X-ray device, the X-ray irradiation region is visually indicated by laser light without having to use a lamp otherwise provided between the X-ray tube and the shutter.

13 Claims, 17 Drawing Sheets

[Fig.1]
PRIOR ART
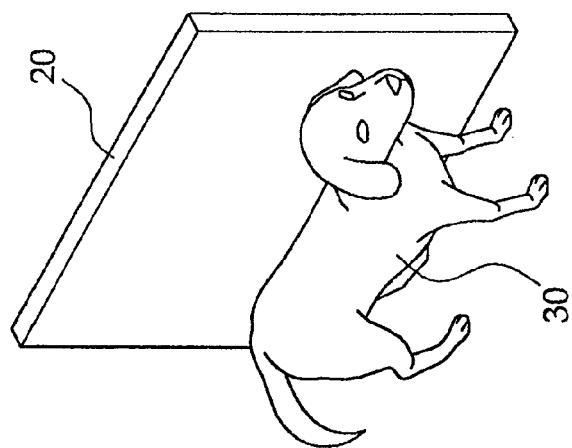
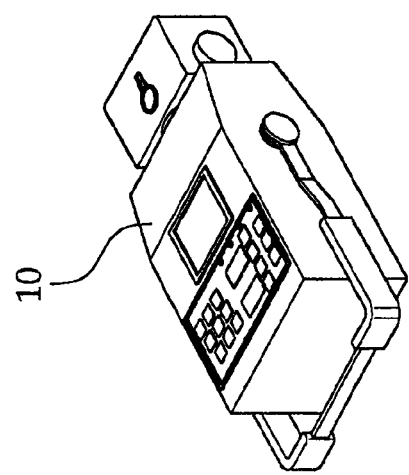

[Fig.2]
PRIOR ART
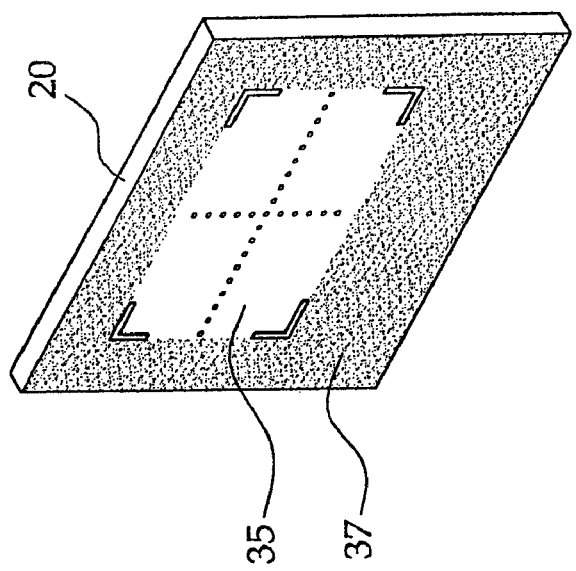
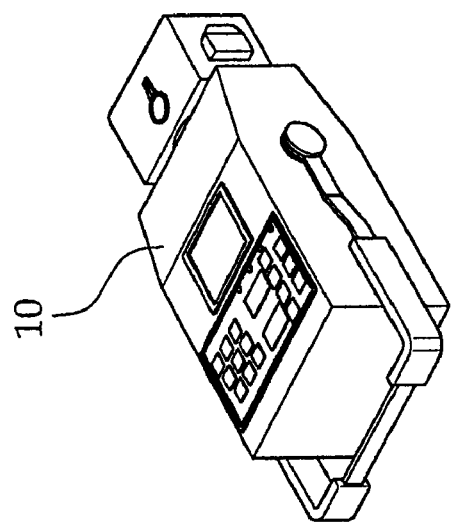

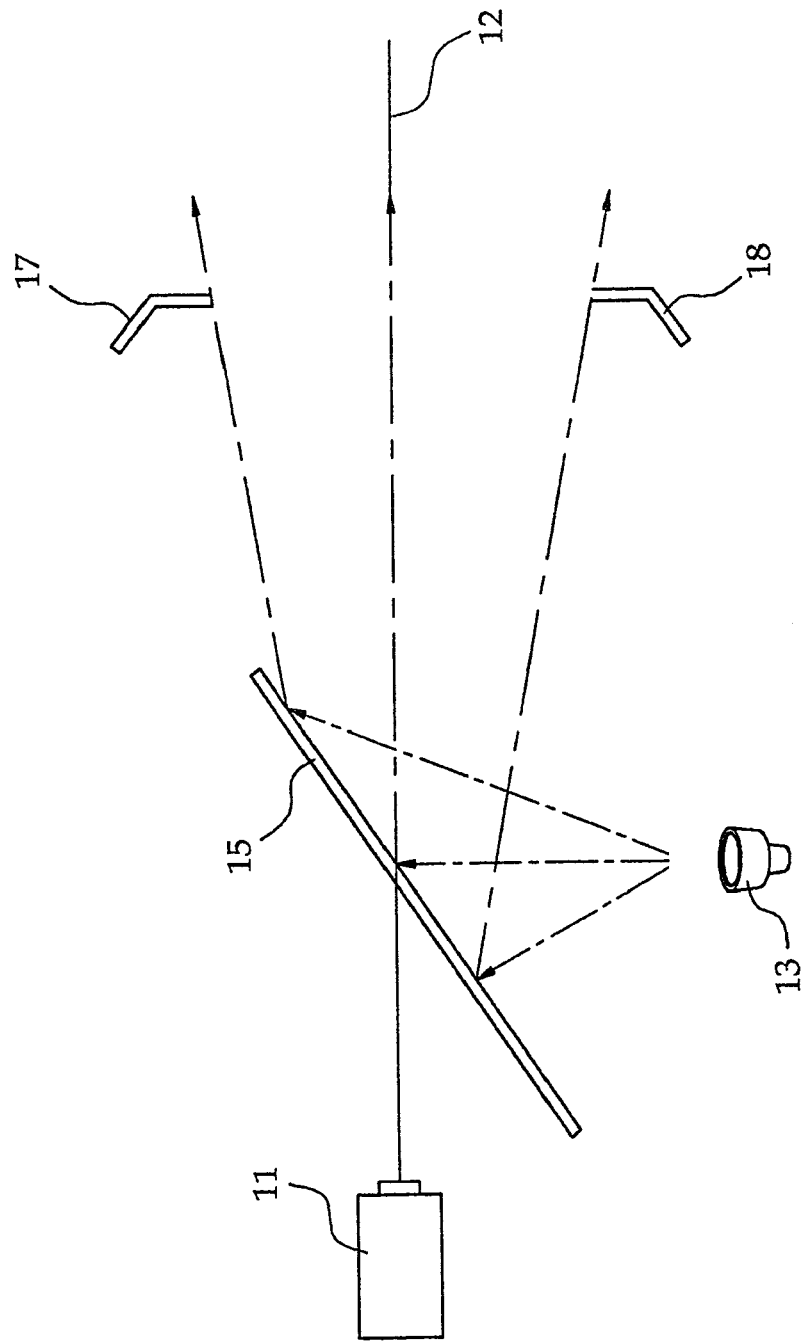
[Fig.3] PRIOR ART

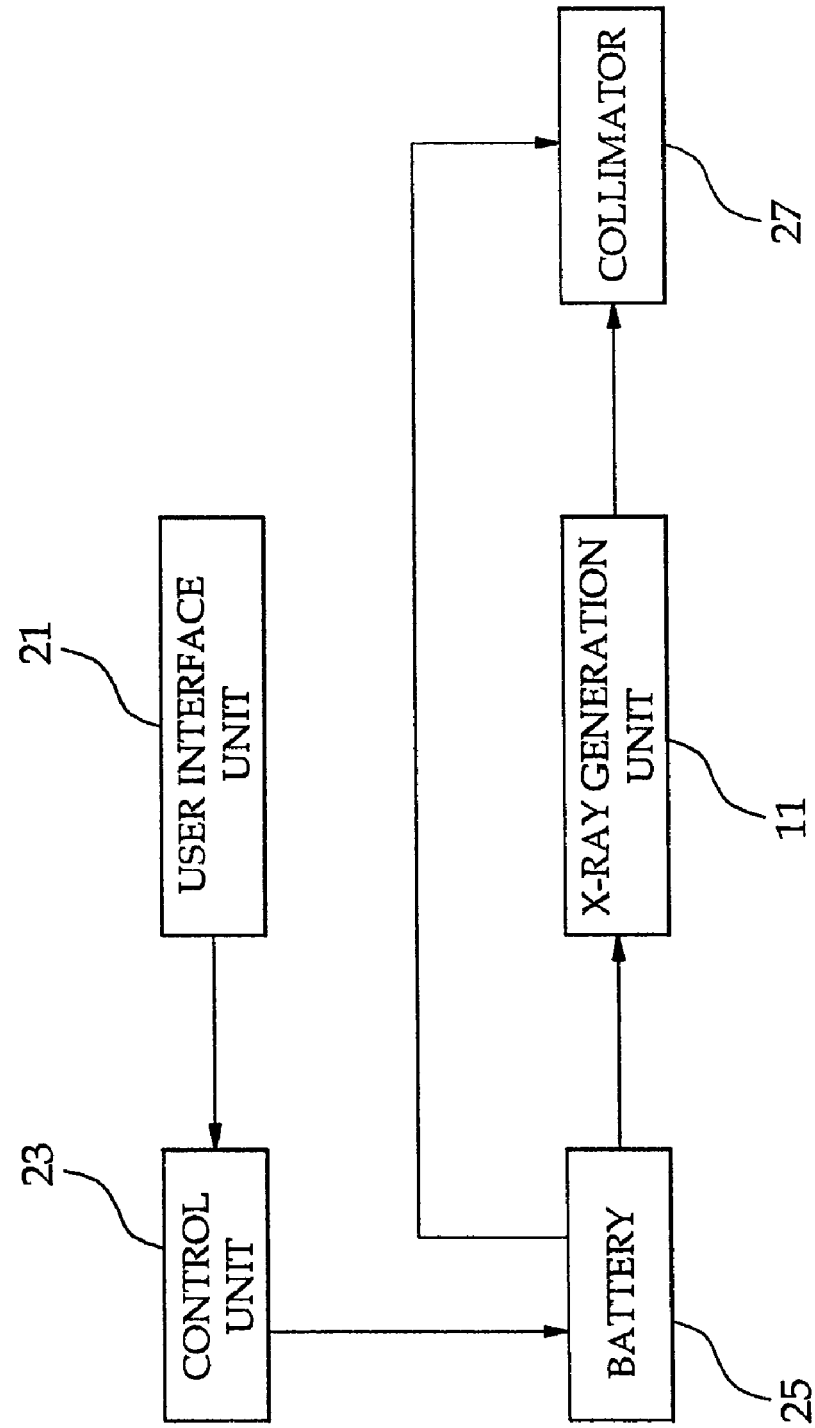

[Fig.5]
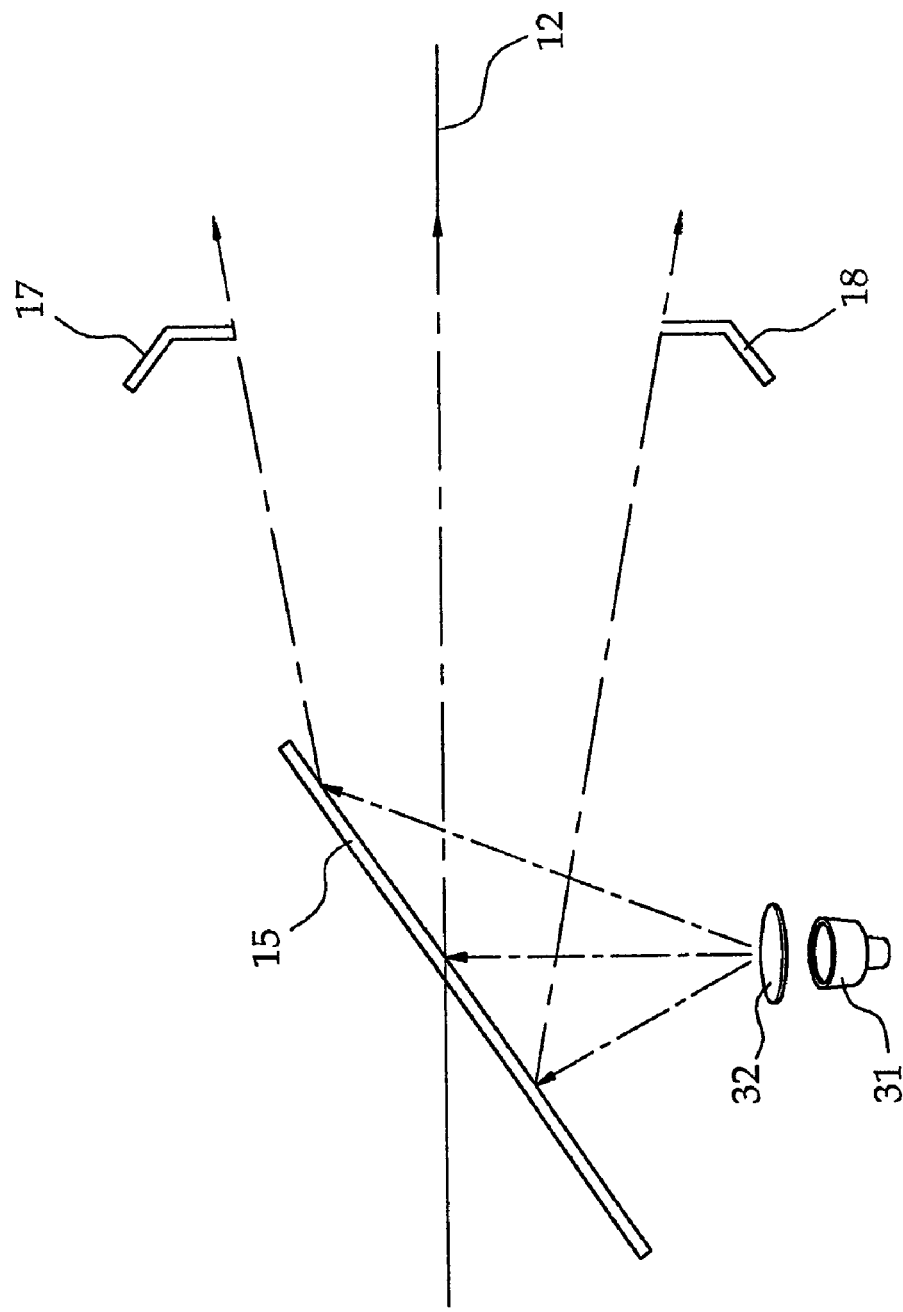

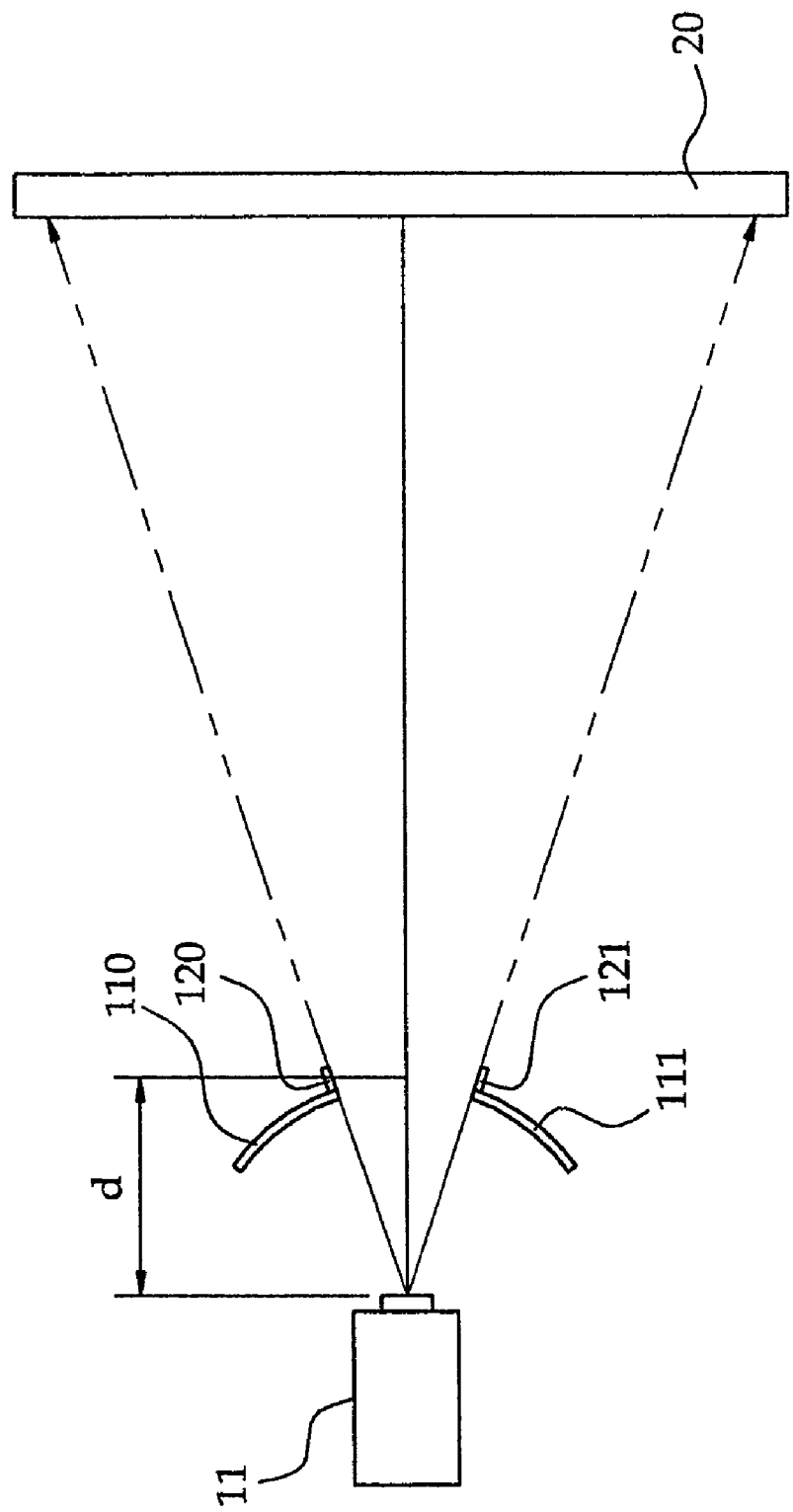
[Fig.6]

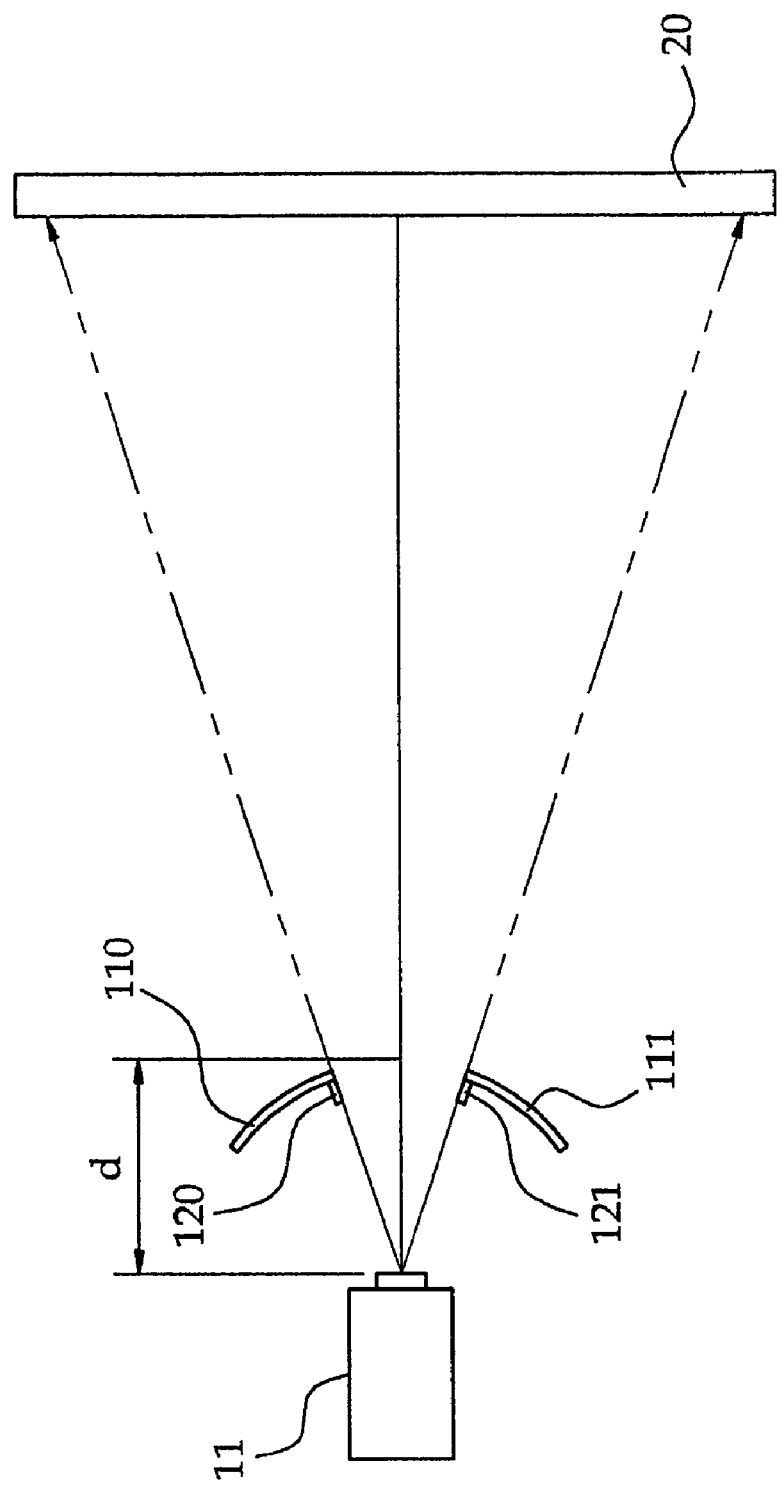
[Fig.7]

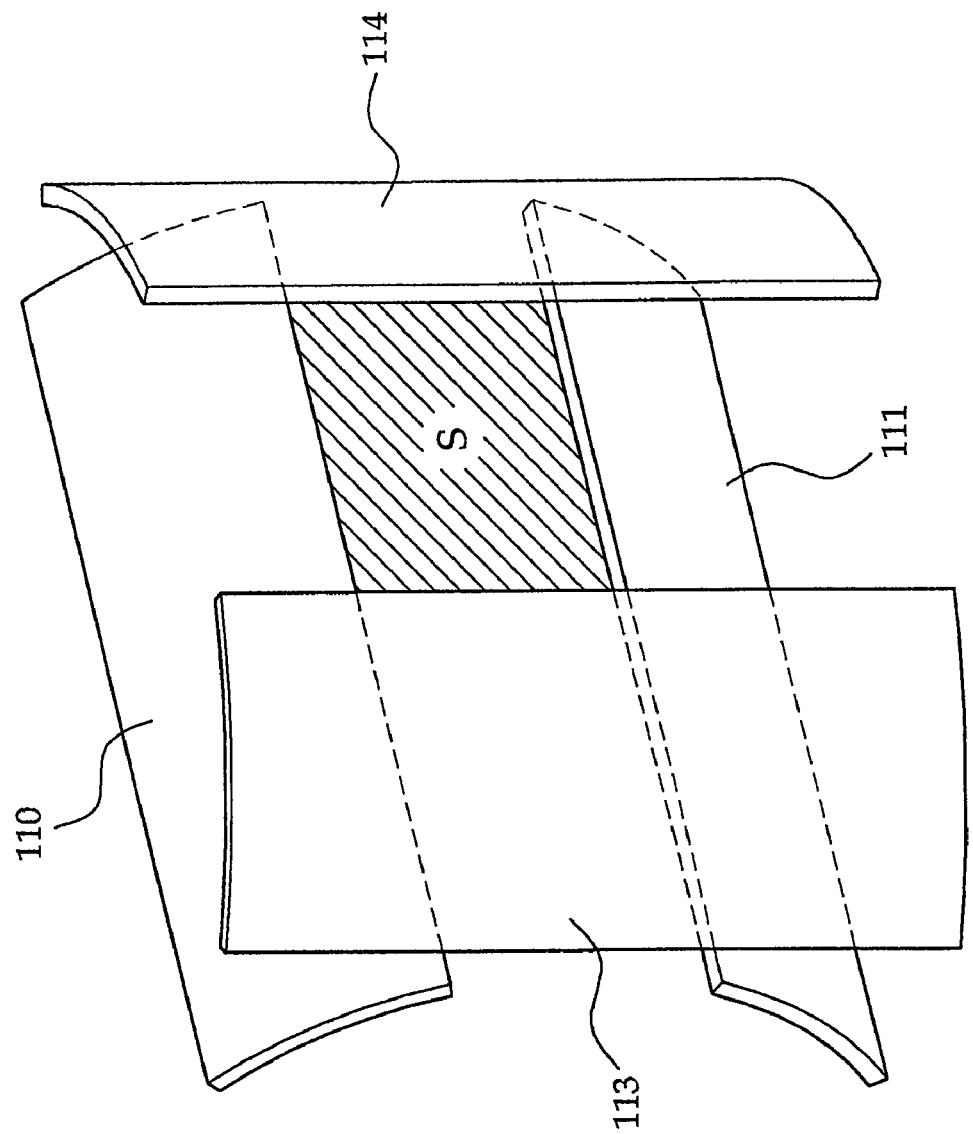
[Fig.8]

【Fig.9a】
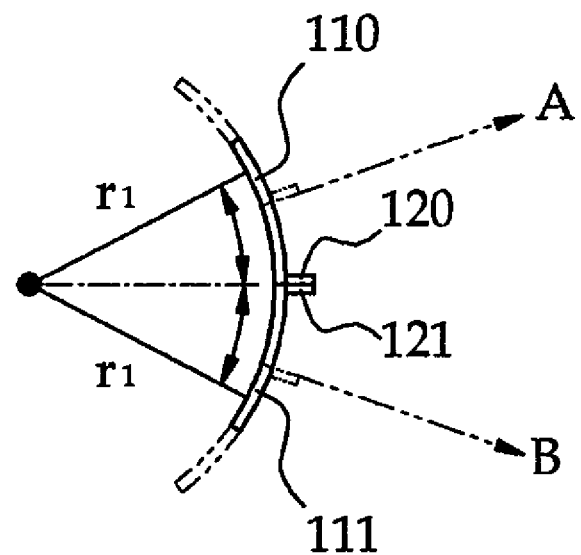
【Fig.9b】
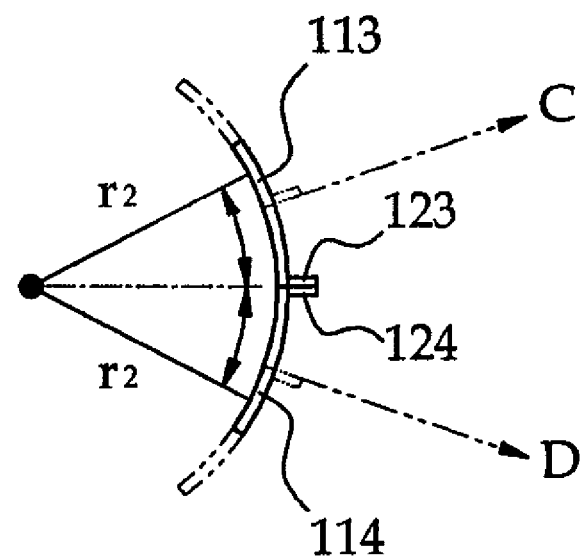

[Fig.10]
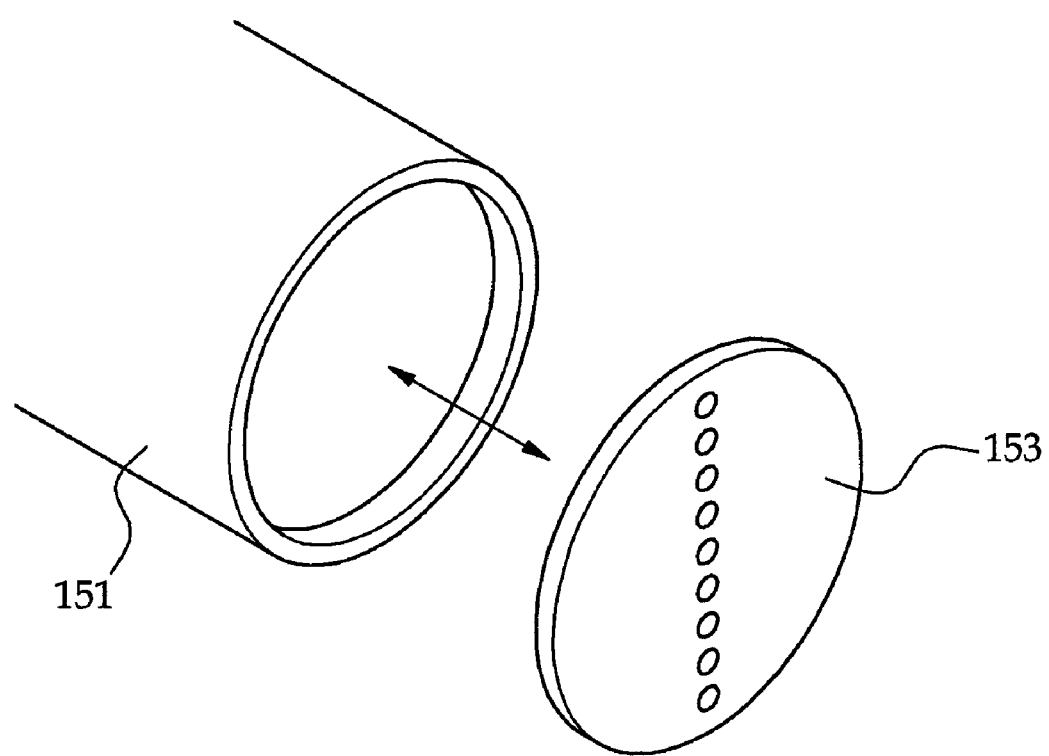

[Fig.11a]
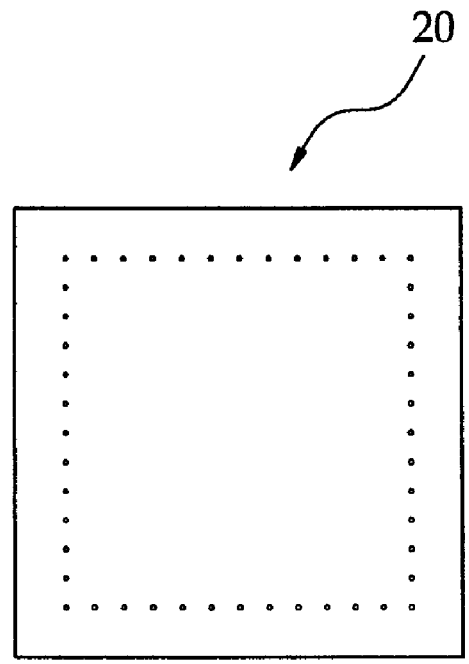
[Fig.11b]
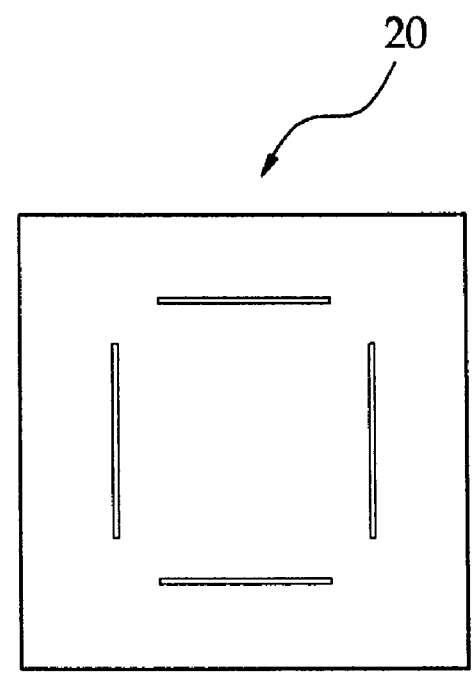

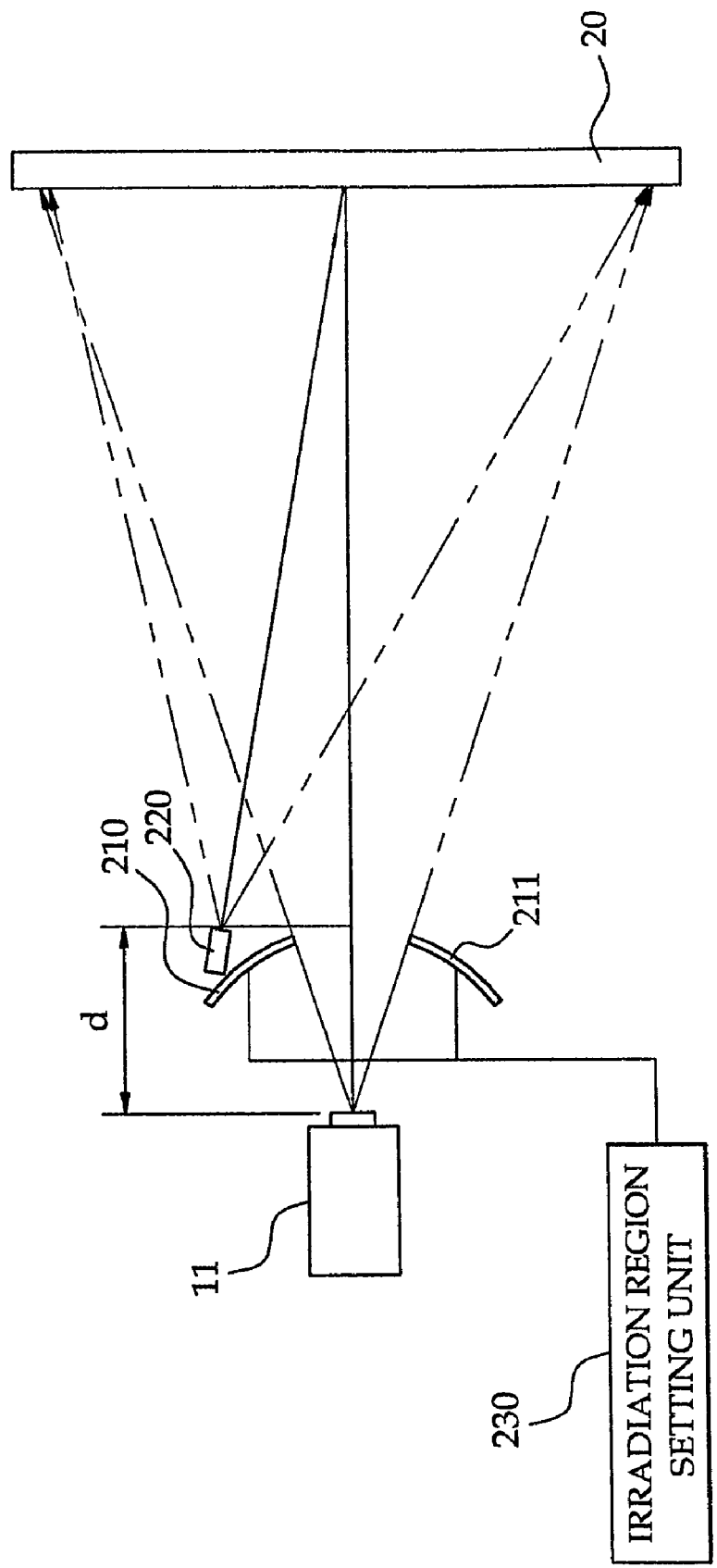

[Fig.13a]
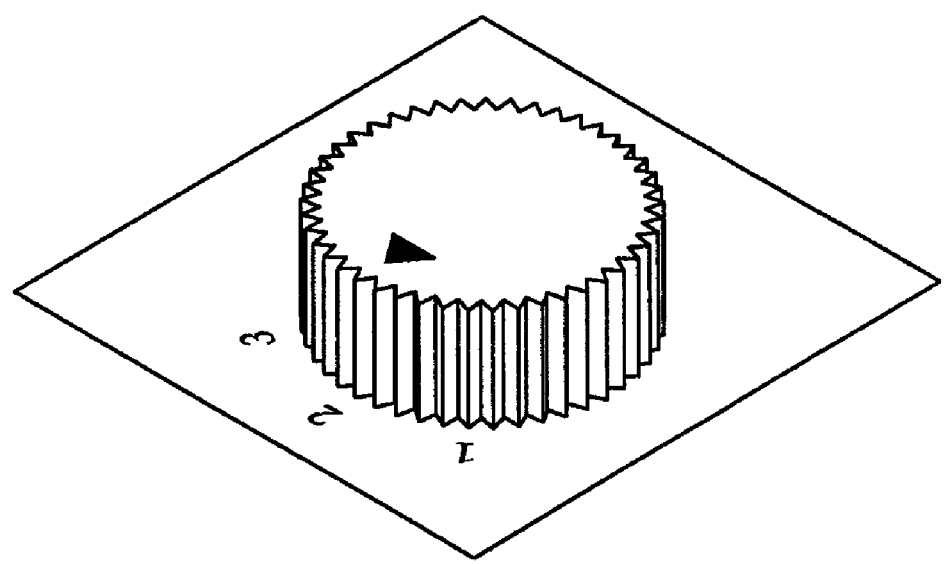
[Fig.13b]
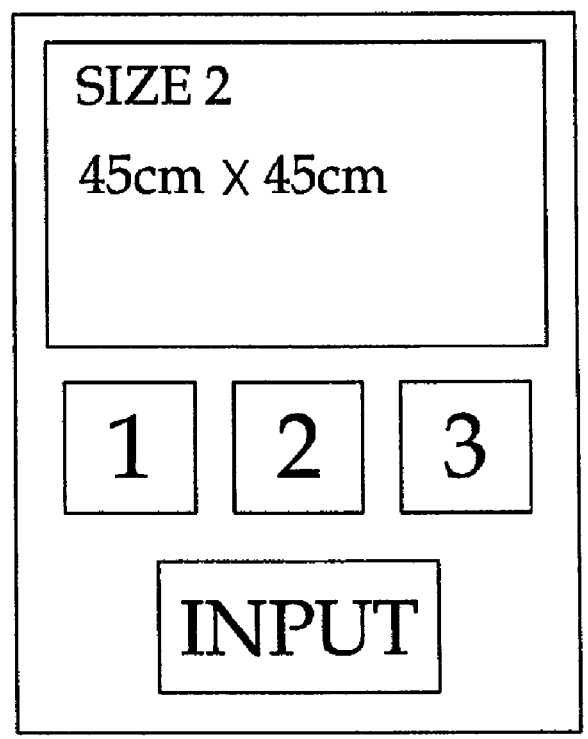

[Fig.14a]
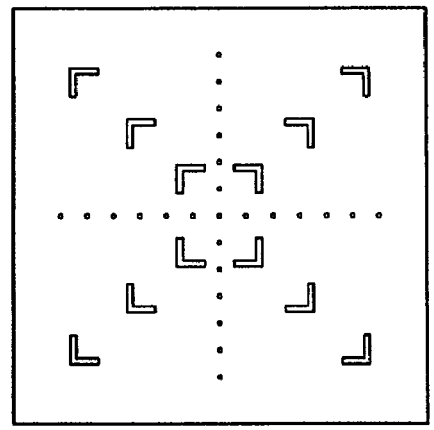
[Fig.14b]
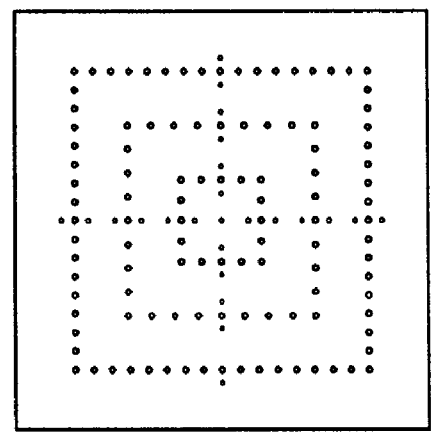
[Fig.14c]
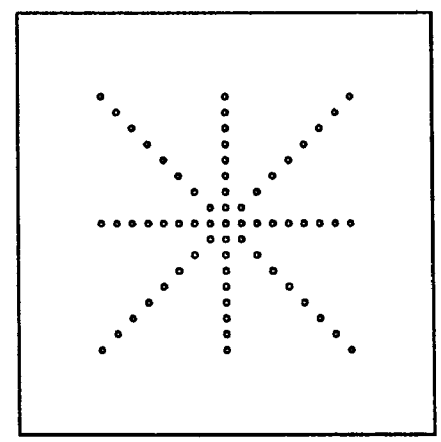

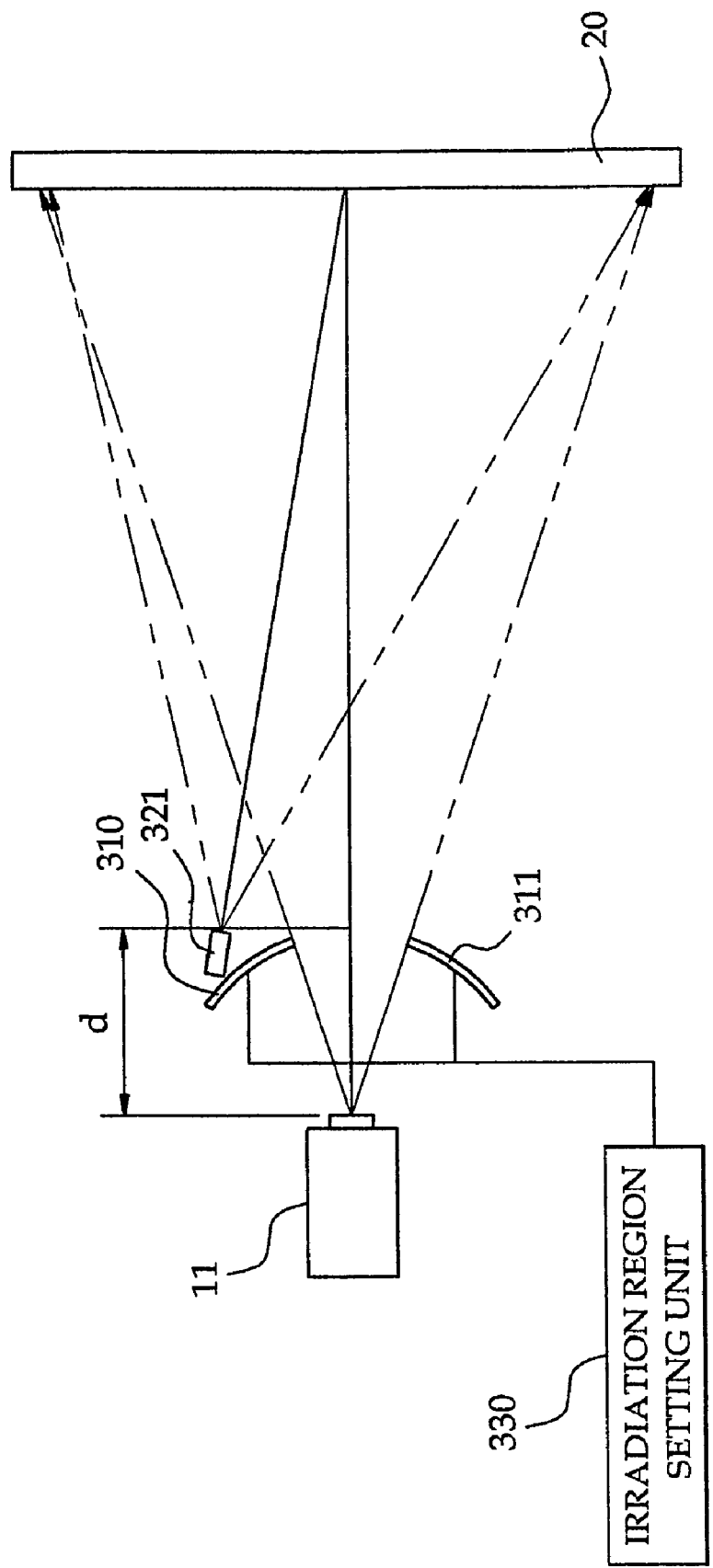

[Fig.16]
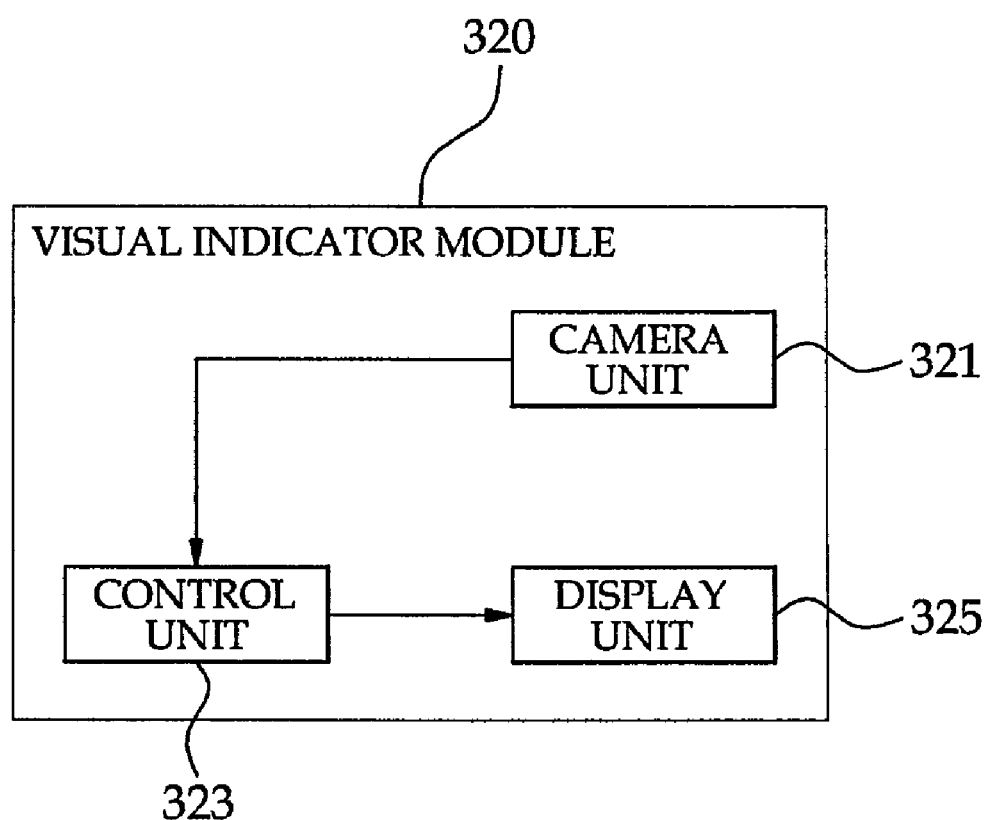

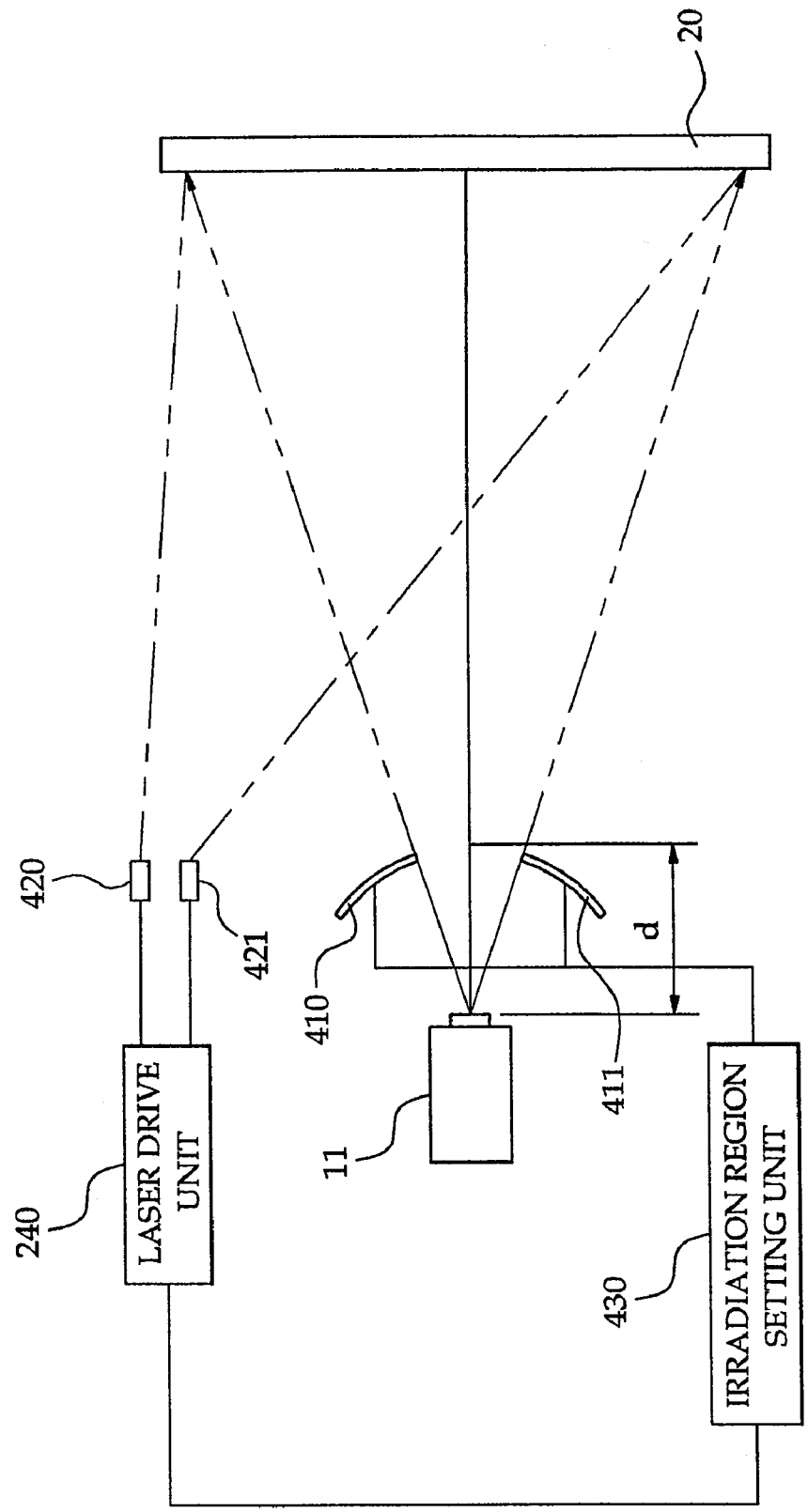
[Fig.17]

COMPACT AND LIGHTWEIGHT X-RAY DEVICE

RELATED APPLICATIONS

The present application is based on, and claims priority from, Korean Application Number 10-2008-0002070, filed Jan. 8, 2008, the disclosure of which is hereby incorporated by reference herein in its entirety.

FIELD OF THE INVENTION

The present invention relates to an X-ray device and, more particularly, to an X-ray device smaller in size and weight than conventional ones, in which device an X-ray irradiation region is visually indicated by laser light without having to use a lamp otherwise provided between an X-ray tube that irradiates a beam of X-rays on an object and a shutter that regulates the irradiation area of the beam of X-rays irradiated on the object.

BACKGROUND OF THE INVENTION

An X-ray device refers to, e.g., a device that diagnoses the health condition of a human patient or an animal by transmitting a beam of X-rays through an object such as the human patient or the animal and acquiring an X-ray image from the beam of X-rays coming out of the object.

Shown in FIG. 1 is a conventional portable X-ray device. Referring to d1, an X-ray device 10 is designed to generate a beam of X-rays and irradiate it on an image capturing unit 20. As the image capturing unit 20, use is made of a digital imaging panel that can capture an X-ray image using an X-ray film or a multiplicity of photo sensors.

An object 30 whose X-ray image is to be captured is positioned between the X-ray device 10 and the image capturing unit 20. The beam of X-rays irradiated from the X-ray device 10 pass through the object 30. Using the beam of X-rays transmitted through the object 30, the image capturing unit 20 captures an X-ray image of the object 30.

In order to obtain an accurate X-ray image of the object 30, there is a need to identify an X-ray irradiation region on the object 30 prior to taking the X-ray image of the object 30. Since the beam of X-rays is not visually recognizable, it is necessary to use an additional unit that enables a user to visually identify the X-ray irradiation region. The unit that enables a user to visually identify and adjust the X-ray irradiation region is typically referred to as a collimator. The collimator serves to direct the light of a lamp toward the X-ray irradiation region, thereby enabling the user to identify the X-ray irradiation region through the lamp light.

FIG. 2 shows an exemplary use of the conventional X-ray device 10 that indicates an X-ray irradiation region with a typical lamp. Referring to FIG. 2, a collimator for indicating an X-ray irradiation region with a lamp is provided within the X-ray device 10. In order to take an X-ray image of an object, the collimator illuminates the light of a lamp on an image capturing unit 20. The light thus illuminated divides the image capturing unit 20 into an illumination region 35 and a non-illumination region 37. The illumination region 35 of the image capturing unit 20 is equivalent to an actual X-ray irradiation region. Based on the illumination region 35, the user can identify the actual X-ray irradiation region and can accurately take an X-ray image of a target portion of an object by positioning the target portion in the illumination region 35.

FIG. 3 schematically depicts the internal construction of the conventional X-ray device in which an X-ray irradiation region is indicated with a typical lamp. Referring to FIG. 3, a reflection mirror 15 having a specified inclination relative to an X-ray irradiation axis 12 is arranged between an X-ray tube 11 that generates and irradiates a beam of X-rays on an object and a shutter 17 and 18 that regulates the irradiation area of the beam of X-rays. A lamp 13 is arranged below the reflection mirror 15 so that the light emitted from the lamp 13 can be illuminated on the reflection mirror 15. Then, the light is reflected by the reflection mirror 15 to move along the X-ray irradiation axis 12. The illumination area of the light moving along the X-ray irradiation axis 12 is regulated by the shutter 17 and 18, after which the light is illuminated on an image capturing unit. The illumination area of the light on the image capturing unit is the same as the X-ray irradiation region over which the beam of X-rays are actually irradiated by the x-ray tube 11. The user can identify the X-ray irradiation region by observing the illumination region of the light illuminated on the image capturing unit.

For the purpose of simplicity in description, FIG. 3 shows only an upper shutter blade 17 for regulating an upper edge of the beam of X-rays irradiated on the object and a lower shutter blade 18 for regulating a lower edge of the beam of X-rays. It should be noted, however, that the X-ray device further includes a left shutter blade for regulating a left edge of the beam of X-rays and a right shutter blade for regulating a right edge of the beam of X-rays.

With the conventional X-ray device stated above, the lamp has to be arranged between the X-ray tube and the shutter in order for the user to identify the X-ray irradiation region. This makes it necessary to provide a lamp-receiving space between the X-ray tube and the shutter. It is also necessary to provide a space and a vent hole for dissipating the heat generated from the lamp. For that reason, the conventional X-ray device is doomed to be fabricated with a greater size and an increased weight. Furthermore, the conventional X-ray device has a problem in that a large amount of electric power is consumed in operating the lamp.

The size of the shutter required to regulate the irradiation area of the beam of X-rays becomes greater as the shutter is positioned farther away from the focal point of the X-ray tube. Typically, the shutter is made of heavy and X-ray impermeable lead that can effectively regulate the irradiation area of the beam of X-rays irradiated on the object. This means that the size and weight of the X-ray device is increased in proportion to the size of the shutter. In case of the conventional X-ray device mentioned above, the distance between the X-ray tube and the focal point must be greater than a specified value to accommodate the lamp and the reflection mirror. This poses a problem in that the conventional X-ray device is constrained to use a shutter having a greater size and an increased weight.

SUMMARY OF THE INVENTION

In view of the above-noted and other problems inherent in the prior art, it is an object of the present invention to provide a compact and lightweight X-ray device in which a laser is used in place of a lamp to reduce heat generation and power consumption in the X-ray device while enabling a user to readily identify an X-ray irradiation region.

Another object of the present invention is to provide a compact and lightweight X-ray device that eliminates the need to use a lamp and a reflection mirror.

In one aspect of the present invention provides, there is provided a collimator for use in an X-ray device, comprising: a shutter arranged around an X-ray irradiation axis for regulating an X-ray irradiation region; a laser pointer generating unit for generating a laser pointer used to indicate the X-ray irradiation region regulated by the shutter; and a reflection mirror arranged on the X-ray irradiation axis in an inclined relationship therewith for reflecting the laser pointer toward the X-ray irradiation region.

In another aspect of the present invention provides, there is provided an X-ray device comprising: an X-ray generation unit for generating a beam of X-rays; a collimator for regulating an X-ray irradiation region on which the beam of X-rays is irradiated, the collimator being designed to indicate the X-ray irradiation region with a laser pointer; and a power source for supplying an electric current to the X-ray generation unit and the collimator.

In a further aspect of the present invention provides, there is provided an X-ray device for irradiating a beam of X-rays on an object to capture an X-ray image of the object, comprising: an X-ray tube for generating the beam of X-rays and irradiating the beam of X-rays on the object; a shutter arranged around an X-ray irradiation axis for regulating an X-ray irradiation region on which the beam of X-rays is irradiated through the object; and a visual indicator unit arranged on the shutter for movement together with the shutter, the visual indicator unit being designed to visually indicate the X-ray irradiation region.

In a still further aspect of the present invention provides, there is provided an X-ray device for irradiating a beam of X-rays on an object to capture an X-ray image of the object, comprising: an X-ray tube for generating the beam of X-rays and irradiating the beam of X-rays on the object; an irradiation region setting unit for presetting the size of an X-ray irradiation region on which the beam of X-rays is irradiated through the object; a shutter arranged around an X-ray irradiation axis for regulating the X-ray irradiation region depending on the size preset by the irradiation region setting unit; and a visual indicator unit arranged on the shutter for visually indicating the X-ray irradiation region.

In a yet still further aspect of the present invention provides, there is provided an X-ray device for irradiating a beam of X-rays on an object to capture an X-ray image of the object, comprising: an X-ray tube for generating the beam of X-rays and irradiating the beam of X-rays on the object; an irradiation region setting unit for presetting the size of an X-ray irradiation region on which the beam of X-rays is irradiated through the object; a shutter arranged around an X-ray irradiation axis for regulating the X-ray irradiation region depending on the size preset by the irradiation region setting unit; a visual indicator unit arranged independently of the shutter for visually indicating the X-ray irradiation region, the visual indicator unit being movable in synchronism with movement of the shutter; and a drive unit associated with the irradiation region setting unit for driving the visual indicator unit in synchronism with movement of the shutter.

With the X-ray device of the present invention, a laser is used in place of a lamp. This makes it possible to reduce heat generation and power consumption in the X-ray device while enabling a user to readily identify an X-ray irradiation region.

With the X-ray device of the present invention, a display unit that enables a user to identify an X-ray irradiation region is arranged in a shutter. Therefore, there is no need to arrange a lamp and a reflection mirror between the X-ray tube and the shutter. This makes it possible to fabricate an X-ray device with a small size and a reduced weight. It is also possible to shorten the distance between the focal point of the X-ray tube and the shutter, which makes it possible reduce the size of the shutter that regulates the irradiation area of the beam of X-rays irradiated on an object.

BRIEF DESCRIPTION OF THE DRAWINGS

The above and other objects and features of the present invention will become apparent from the following description of preferred embodiments, given in conjunction with the accompanying drawings, in which:

FIG. 1 illustrates a conventional portable X-ray device;

FIG. 2 shows an exemplary use of the conventional X-ray device that indicates an X-ray irradiation region with a typical lamp;

FIG. 3 schematically depicts the internal construction of the conventional X-ray device in which an X-ray irradiation region is indicated with a typical lamp;

FIG. 4 is a functional block diagram showing a portable X-ray device provided with a collimator;

FIG. 5 schematically illustrates the internal construction of an X-ray device with a laser pointer collimator in accordance with a first embodiment of the present invention;

FIG. 6 schematically illustrates the internal construction of an X-ray device in accordance with a second embodiment of the present invention, in which a laser irradiation unit is arranged on the rear surface (at the outer side) of a shutter;

FIG. 7 schematically shows a modified example of the X-ray device in accordance with the second embodiment of the present invention, in which the laser irradiation unit is arranged on the front surface (at the inner side) of the shutter.

FIGS. 8, 9A and 9B are views for specifically explaining the shutter employed in the present invention;

FIG. 10 is a view schematically showing the laser irradiation unit;

FIGS. 11A and 11B are views illustrating different examples of a laser identification mark;

FIG. 12 schematically shows the internal construction of an X-ray device in accordance with a third embodiment of the present invention, which is provided with a laser irradiation unit;

FIGS. 13A and 13B illustrate different examples of an irradiation region setting unit;

FIGS. 14A, 14B and 14C illustrate different examples of a laser identification mark appearing on an image capturing unit;

FIG. 15 schematically shows a modified example of the X-ray device in accordance with the third embodiment of the present invention, in which a camera unit is used in place of the laser irradiation unit;

FIG. 16 is a functional block diagram showing a visual indicator module employed in the X-ray device shown in FIG. 15;

FIG. 17 schematically shows the internal construction of an X-ray device in accordance with a fourth embodiment of the present invention, which is provided with an independently arranged laser irradiation unit.

DETAILED DESCRIPTION OF THE PREFERRED EMBODIMENTS

Hereinafter, certain embodimefnts of an X-ray device in accordance with the present invention will be described in detail with reference to the accompanying drawings.

FIG. 4 is a functional block diagram showing a portable X-ray device provided with a collimator. Referring to FIG. 4, a user command for preliminarily identifying an X-ray irradiation region is inputted though a user interface 21 prior to taking an X-ray image of an object. Responsive to the user command thus inputted, a control unit 23 causes a battery 25 to supply an electric current to a collimator 27. Using the electric current, the collimator 27 generates a laser pointer with a specific pattern and directs the laser pointer toward an image capturing unit 20 (see FIGS. 6 and 7). The laser pointer appearing on the image capturing unit 20 enables the user to identify an X-ray irradiation region prior to taking an image of the object.

A target portion of the object is positioned in the X-ray irradiation region identified through the laser pointer. Then, a user command for taking the image of the object is inputted through the user interface 21. In response to the user command thus inputted, the control unit 23 causes the battery 25 to supply an electric current to an X-ray generation unit 11. Using the electric current, the X-ray generation unit 11 generates a beam of X-rays and irradiates it toward the image capturing unit 20 so that the image capturing unit 20 can take an X-ray image of the object.

FIG. 5 schematically illustrates the internal construction of an X-ray device with a laser pointer collimator in accordance with a first embodiment of the present invention. Referring to FIG. 5, the X-ray device includes a laser light generator unit 31 which is supplied with an electric current to generate laser light. Examples of the laser light generator 31 include: a solid-state laser in which the crystals of artificial ruby, glass or YAG (yttrium aluminum garnet) containing chromium ions are used as a laser light generating material; a gas-state laser in which a mixture gas of helium and neon, argon, krypton, carbon dioxide or a mixture gas of helium and nitrogen is used as a laser light generating material; and a semiconductor laser in which laser light is generated by allowing an electric current to flow through a p-n junction diode consisting of p-type and n-type gallium arsenide semiconductors. Preferably, the laser light generator 31 is supplied with an electric current from the battery 25.

The X-ray device includes a patterning lens 32 having a plurality of through-holes formed in a specified pattern. The laser light generated in the laser light generator 31 is transmitted through the through-holes so that the laser light corresponding to the pattern of the through-holes can be irradiated on a reflection mirror 15. The reflection mirror 15 is positioned on an X-ray irradiation axis 12 in an inclined relationship with respect thereto and serves to reflect the laser light coming from the patterning lens 32 in the same direction as the X-ray irradiation axis 12.

The X-ray device includes a shutter for regulating an X-ray irradiation region. The shutter includes shutter blades 17 and 18 symmetrically arranged above and below the X-ray irradiation axis 12. Typically, shutter blades for regulating the length of the X-ray irradiation region and shutter blades for regulating the width of the X-ray irradiation region are symmetrically arranged at the upper, lower, left and right sides of the X-ray irradiation axis 12. For the purpose of convenience in description, however, only the shutter blades 17 and 18 arranged at the upper and lower sides of the X-ray irradiation axis 12 are shown in FIG. 5. The X-ray irradiation region is changed by increasing or decreasing the gap size between the shutter blades 17 and 18. The illumination area of the laser light reflected from the reflection mirror 15 is regulated by the shutter blades 17 and 18. The illumination area of the laser light is substantially the same as the X-ray irradiation region.

FIG. 6 schematically illustrates the internal construction of an X-ray device in accordance with a second embodiment of the present invention. Referring to FIG. 6, the beam of X-rays generated in an X-ray tube 11 is irradiated on the image capturing unit 20. A shutter for regulating the X-ray irradiation region is arranged in front of the X-ray tube 11 along the X-ray irradiation direction. It is preferred that the distance d between the focal point of the X-ray tube 11 and the shutter is as small as possible.

The shutter includes an upper shutter blade 110 for regulating the upper edge of the X-ray irradiation region and a lower shutter blade 111 for regulating the lower edge of the X-ray irradiation region. Although only the upper and lower shutter blades 110 and 111 are shown in FIG. 6 for the purpose of convenience in description, it should be appreciated that the shutter further includes left and right shutter blades for regulating the left and right edges of the X-ray irradiation region. The beam of X-rays emitted from the X-ray tube 11 is irradiated on the image capturing unit 20 through the shutter, at which time the X-ray irradiation region on the image capturing unit 20 are regulated by the upper, lower, left and right shutter blades.

Laser irradiation units 120 and 121, which constitute a visual indicator unit defined in the claims, are attached to the rear surfaces (the outer sides) of the upper shutter blade 110 and the lower shutter blade 111 opposite from the X-ray tube 11. The laser irradiation unit 120 attached to the upper shutter blade 110 emits laser light along the upper edge of the beam of X-rays irradiated on the image capturing unit 20 through the shutter. The laser irradiation unit 121 attached to the lower shutter blade 111 emits laser light along the lower edge of the beam of X-rays irradiated on the image capturing unit 20 through the shutter. The laser light emitted from the laser irradiation units 120 and 121 indicates the upper and lower edges of the X-ray irradiation region on the image capturing unit 20.

Similarly, laser irradiation units (not shown) are attached to the rear surfaces (the outer sides) of the left shutter blade and the right shutter blade opposite from the X-ray tube 11. The laser irradiation unit attached to the left shutter blade emits laser light along the upper edge of the beam of X-rays irradiated on the image capturing unit 20 through the shutter. The laser irradiation unit attached to the right shutter blade emits laser light along the right edge of the beam of X-rays irradiated on the image capturing unit 20 through the shutter. The laser light emitted from the laser irradiation units attached to the left and right shutter blades indicates the left and right edges of the X-ray irradiation region on the image capturing unit 20.

FIG. 7 schematically shows a modified example of the X-ray device in accordance with the second embodiment of the present invention. The X-ray device shown in FIG. 7 is essentially the same as the X-ray device illustrated in FIG. 6, except that the laser irradiation units 120 and 121 are attached to the front surfaces (the inner sides) of the upper shutter blade 110 and the lower shutter blade 111 that face toward the X-ray tube 11. This holds true in case of the laser irradiation units attached to the left shutter blade and the right shutter blade.

FIGS. 8, 9A and 9B are views for specifically explaining the shutter employed in the present invention. Referring to FIG. 8, a first shutter includes an upper shutter blade 110 and a lower shutter blade 111, both of which serve to shift the X-ray irradiation region in the vertical direction. A second shutter includes a left shutter blade 113 and a right shutter blade 114, both of which serve to shift the X-ray irradiation region in the lateral direction. The first and second shutters are moved vertically and laterally in an overlapped state to form an aperture S of varying size that defines the X-ray irradiation region.

The movement of the first and second shutters will be described in detail with reference to FIGS. 9A and 9B. Referring first to FIG. 9A which is a side view of the shutters, the upper shutter blade 110 and the lower shutter blade 111 of the first shutter are curved to have a first radius r1 from the focal point of the beam of X-rays. The upper shutter blade 110 and the lower shutter blade 111 are movable upwards or downwards along the arc of a circle with the first radius r1. The laser irradiation units 120 and 121 are attached to the lower end of the upper shutter blade 110 and the upper end of the lower shutter blade 111, respectively. As the upper shutter blade 110 and the lower shutter blade 111 move upwards or downwards along the arc, the laser irradiation units 120 and 121 are also moved along the same trajectory as that of the upper shutter blade 110 and the lower shutter blade 111. The laser irradiation unit 120 attached to the upper shutter blade 110 emits laser light in the direction A along the upper edge of the beam of X-rays to indicate the upper edge of the X-ray irradiation region on the image capturing unit 20. The laser irradiation unit 121 attached to the upper shutter blade 111 emits laser light in the direction B along the lower edge of the beam of X-rays to indicate the lower edge of the X-ray irradiation region on the image capturing unit 20.

Referring next to FIG. 9B which is a top plan view of the shutters, the left shutter blade 113 and the right shutter blade 114 of the second shutter are curved to have a second radius r2 from the focal point of the beam of X-rays. The left shutter blade 113 and the right shutter blade 114 are movable to the left or the right along the arc of a circle with the second radius r2. Laser irradiation units 123 and 124 are attached to the right end of the left shutter blade 113 and the left end of the right shutter blade 114, respectively. As the left shutter blade 113 and the right shutter blade 114 move to the left or the right along the arc, the laser irradiation units 123 and 124 are also moved along the same trajectory as that of the left shutter blade 113 and the right shutter blade 114. The laser irradiation unit 123 attached to the left shutter blade 113 emits laser light in the direction C along the left edge of the beam of X-rays to indicate the left edge of the X-ray irradiation region on the image capturing unit 20. The laser irradiation unit 124 attached to the right shutter blade 114 emits laser light in the direction D along the right edge of the beam of X-rays to indicate the right edge of the X-ray irradiation region on the image capturing unit 20.

FIG. 10 schematically shows the construction of the laser irradiation unit. Referring to FIG. 10, the laser irradiation unit includes a laser light generator 151 for generating laser light and a patterning lens 153 for changing the laser light into a specified pattern before it is irradiated on the image capturing unit. The laser light generator 151 may be a solid-state laser, a gas-state laser or a semiconductor laser, the classification of which depends on the material used and the mode of operation. The patterning lens 153 has a plurality of through-holes arranged in a predetermined pattern and designed to create a laser identification mark that indicates the upper, lower, left or right edges of the X-ray irradiation region. The laser light generated in the laser light generator 151 is split into an array of light beams of a predetermined pattern while passing through the through-holes of the patterning lens 153. Then the array of light beams is irradiated on the image capturing unit and is used as the laser identification mark that indicates the X-ray irradiation region. FIGS. 11A and 11B illustrate different examples of the laser identification mark formed on the image capturing unit 20 by the array of light beams passing through the through-holes of the patterning lens 153.

While the laser light is employed to indicate the X-ray irradiation region in the foregoing embodiments, it may also be possible to use other coherent light depending on the application of the present invention. This also falls within the scope of the present invention.

FIG. 12 schematically shows the internal construction of an X-ray device in accordance with a third embodiment of the present invention. Referring to FIG. 12, the beam of X-rays generated in the X-ray tube 11 is irradiated on the image capturing unit 20. A shutter for regulating the X-ray irradiation region is arranged in front of the X-ray tube 11 along the X-ray irradiation direction. It is preferred that the distance d between the focal point of the X-ray tube 11 and the shutter is as small as possible.

The shutter includes an upper shutter blade 210 for regulating the upper edge of the X-ray irradiation region and a lower shutter blade 211 for regulating the lower edge of the X-ray irradiation region. Although only the upper and lower shutter blades 210 and 211 are shown in FIG. 12 for the purpose of convenience in description, it should be appreciated that the shutter further includes left and right shutter blades for regulating the left and right edges of the X-ray irradiation region.

The upper and lower shutter blades 210 and 211 and the left and right shutter blades are moved vertically and laterally depending on the size of the X-ray irradiation region preset by an irradiation region setting unit 230. The irradiation region setting unit 230 includes a setting part for presetting the size of the X-ray irradiation region and a drive part for driving the shutter depending on the size of the X-ray irradiation region preset by the setting part. Although not shown in the drawings, the drive part includes a plurality of gears operatively connected to the shutter and an electric motor for rotating the gears.

Depending on the size of the X-ray irradiation region preset by the setting part, the drive part displaces the upper and lower shutter blades 210 and 211 and the left and right shutter blades to form an aperture corresponding to the X-ray irradiation region on the image capturing unit 20.

FIGS. 13A and 13B illustrate different examples of the setting part of the irradiation region setting unit 230. In one example of the setting part illustrated in FIG. 13A, a rotary knob is mounted to a housing of the X-ray device. A reference mark that indicates the current size of the X-ray irradiation region is placed on the top surface of the rotary knob. A plurality of graduations "1", "2" and "3" that indicates the varying size of the X-ray irradiation region is placed on the housing 61 of the X-ray device. The size of the X-ray irradiation region can be arbitrarily set by turning the rotary knob so that the reference mark on the rotary knob can be aligned with one of the graduations "1", "2" and "3."

In another example of the setting part illustrated in FIG. 13B, the setting part includes a display and a keypad arranged on the surface of the housing of the X-ray device. The key pad includes a plurality of size selection keys "1", "2" and "3" that can be pressed to select the size of the X-ray irradiation region and an input key that can be pressed to input the size of the X-ray irradiation region selected. If a user presses, e.g., the size selection key "2", the length and width of the X-ray irradiation region is displayed on the display to read, e.g., "SIZE 2, 45 cm×45 cm". Then the user presses the input key to finalize the task of selecting the size of the X-ray irradiation region.

Referring again to FIG. 12, a laser irradiation unit 220 is arranged on the opposite side of the upper shutter blade 210 from the X-ray tube 11. The laser irradiation unit 220 irradiates laser light toward the image capturing unit 20 to indicate the X-ray irradiation region whose size has been selected by the irradiation region setting unit 230.

FIGS. 14A, 14B and 14C illustrate different examples of the laser identification mark appearing on the image capturing unit. Referring to FIGS. 14A and 14B, the size of the X-ray irradiation region preset through the use of the irradiation region setting unit 230 is indicated on the image capturing unit 20 by irradiating the laser light to form a laser identification mark having an angle bracket shape or a square shape. Turning to FIG. 14C, the size of the X-ray irradiation region preset through the use of the irradiation region setting unit 230 is indicated on the image capturing unit 20 by irradiating the laser light to form a laser identification mark having a dot axis shape.

Referring again to FIG. 12, it is preferred that the laser irradiation unit 220 is arranged in a position nearest to the shutter insofar as it does not interrupt the beam of X-rays irradiated toward the image capturing unit 20 through the shutter. The laser irradiation unit 220 is fixedly arranged on the opposite surface of the shutter from the X-ray tube 11 so that the deviation between the actual X-ray irradiation region actually irradiated by the beam of X-rays and the target X-ray irradiation region indicated by the laser identification mark is equal to or smaller than a first threshold value.

If the user presets the X-ray irradiation region through the use of the irradiation region setting unit 230, the shutter blades are moved to ensure that the beam of X-rays is irradiated on the preset X-ray irradiation region. The user can determine the actual X-ray irradiation region by observing the laser identification mark mapped to the size of the preset X-ray irradiation region.

FIG. 15 schematically shows a modified example of the X-ray device in accordance with the third embodiment of the present invention, in which a camera unit 321 is used in place of the laser irradiation unit 220. Referring to FIG. 15, the beam of X-rays generated in the X-ray tube 11 is irradiated toward the image capturing unit 20. A shutter for regulating the X-ray irradiation region is arranged in front of the X-ray tube 11 along the X-ray irradiation direction. It is preferred that the distance d between the focal point of the X-ray tube 11 and the shutter is as small as possible.

The shutter includes an upper shutter blade 310 for regulating the upper edge of the X-ray irradiation region and a lower shutter blade 311 for regulating the lower edge of the X-ray irradiation region. Although only the upper and lower shutter blades 310 and 311 are shown in FIG. 15 for the purpose of convenience in description, it should be appreciated that the shutter further includes left and right shutter blades for regulating the left and right edges of the X-ray irradiation region.

The upper and lower shutter blades 310 and 311 and the left and right shutter blades are moved vertically and laterally depending on the size of the X-ray irradiation region preset by an irradiation region setting unit 330. The irradiation region setting unit 330 includes a setting part for presetting the size of the X-ray irradiation region and a drive part for driving the shutter depending on the size of the X-ray irradiation region preset by the setting part. Although not shown in the drawings, the drive part includes a plurality of gears operatively connected to the shutter and an electric motor for rotating the gears.

Depending on the size of the X-ray irradiation region preset by the setting part, the drive part displaces the upper and lower shutter blades 210 and 211 and the left and right shutter blades to form an aperture corresponding to the X-ray irradiation region on the image capturing unit 20.

A camera unit 321 is arranged on the opposite surface of the shutter from the X-ray tube 11. The camera unit 321 is designed to take an image of the X-ray irradiation region on the image capturing unit 20.

It is preferred that the camera unit 321 is arranged in a position nearest to the shutter insofar as it does not interrupt the beam of X-rays irradiated toward the image capturing unit 20 through the shutter. The camera unit 321 is fixedly arranged on the opposite surface of the shutter from the X-ray tube 11 so that the deviation between the actual X-ray irradiation region actually irradiated by the beam of X-rays and the target X-ray irradiation region taken by the camera unit 321 is equal to or smaller than a first threshold value.

FIG. 16 is a functional block diagram showing a visual indicator module employed in the X-ray device shown in FIG. 15. Referring to FIG. 16, the visual indicator that forms a part of the X-ray device includes a camera unit 321 for taking an image of the X-ray irradiation region, a display unit 325 for displaying an actual X-ray irradiation region and a control unit 323 responsive to a user command inputted through a setting unit for controlling the display unit 325 to display the actual X-ray irradiation region extracted from the image of the X-ray irradiation region.

The control unit 323 is supplied with the image of the X-ray irradiation region taken by the camera unit 321. Responsive to the user command inputted through the setting unit, the control unit 323 identifies the actual X-ray irradiation region contained in the image of the X-ray irradiation region. Then the control unit 323 controls the display unit 325 to display the actual X-ray irradiation region with or without an identification mark.

FIG. 17 schematically shows the internal construction of an X-ray device in accordance with a fourth embodiment of the present invention, which is provided with an independently arranged laser irradiation unit. As shown in FIG. 17, the X-ray device includes laser irradiation units 420 and 421 arranged independently of the shutter. The X-ray device further includes an irradiation region setting unit 430 that displaces the upper and lower shutter blades 410 and 411 and the left and right shutter blades to form an aperture corresponding to the X-ray irradiation region preset by the user. The X-ray device further includes a laser drive unit 240 associated with the irradiation region setting unit 430. The laser drive unit 240 controls the laser irradiation units 420 and 421 in synchronism with the movement of the shutter. In other words, the laser irradiation units 420 and 421 are controlled by the laser drive unit 240 to irradiate a beam of X-rays toward the image capturing unit 20 so that a laser identification mark indicating the X-ray irradiation region preset through the use of the irradiation region setting unit 430 can be displayed on the image capturing unit 20.

The X-ray device of the foregoing embodiments may be operated through the use of a general computer having a computer-readable medium that stores a program needed to operate the X-ray device. Examples of the computer-readable medium include a magnetic storage medium (e.g., a ROM, a floppy disk and a hard disk), an optical recording medium (e.g., a CD ROM and a DVD) and a carrier wave (e.g., transmission through the Internet).

While certain preferred embodiments of the present invention have been described hereinabove, the present invention is not limited thereto. It will be understood by those skilled in the art that various changes and modifications may be made without departing from the scope of the invention defined in the claims.

What is claimed is:

1. A collimator for use in an X-ray device, comprising:
    a shutter arranged around an X-ray irradiation axis configured to regulate an X-ray irradiation region; and
    a laser pointer configured to generate a laser identification mark to indicate the X-ray irradiation region regulated by the shutter, the laser pointer being movable in synchronism with movement of the shutter.

2. The collimator as recited in claim 1, wherein the laser pointer comprises a laser light generator configured to generate laser light and a patterning lens for converting the laser light into the laser identification mark having a specified pattern.

3. The collimator as recited in claim 2, wherein the patterning lens has a plurality of through-holes arranged in a predetermined pattern.

4. An X-ray device comprising:
an X-ray generation unit configured to generate a beam of X-rays;
a collimator configured to regulate an X-ray irradiation region on which the beam of X-rays is irradiated; and
a power source configured to supply electric energy to the X-ray generation unit and the collimator,
wherein the collimator comprises:
a shutter arranged around an X-ray irradiation axis for regulating the X-ray irradiation region; and
a laser pointer configured to generate a laser identification mark to indicate the X-ray irradiation region regulated by the shutter, the laser pointer being movable in synchronism with movement of the shutter.

5. An X-ray device for irradiating a beam of X-rays on an object to capture an X-ray image of the object, comprising:
an X-ray tube for generating the beam of X-rays and irradiating the beam of X-rays on the object;
a shutter arranged around an X-ray irradiation axis for regulating an X-ray irradiation region on which the beam of X-rays is irradiated through the object; and
a visual indicator unit arranged on the shutter for movement together with the shutter, the visual indicator unit being configured to visually indicate the X-ray irradiation region.

6. The X-ray device as recited in claim 5, wherein the shutter comprises:
a first shutter including an upper shutter blade for regulating an upper edge of the X-ray irradiation region and a lower shutter blade for regulating a lower edge of the X-ray irradiation region; and
a second shutter including a left shutter blade for regulating a left edge of the X-ray irradiation region, and a right shutter blade for regulating a right edge of the X-ray irradiation region, and
wherein the visual indicator unit comprises a plurality of laser irradiation units for visually indicating the X-ray irradiation region with laser light, the laser irradiation units being arranged on the shutter blades of the first shutter and the second shutter for movement together with the shutter blades.

7. The X-ray device as recited in claim 6, wherein the shutter blades of the first shutter and the second shutter are movable along an arc about a focal point of the X-ray tube.

8. An X-ray device for irradiating a beam of X-rays on an object to capture an X-ray image of the object, comprising:
an X-ray tube configured to generate the beam of X-rays and configured to irradiate the beam of X-rays on the object;
an irradiation region setting unit configured to preset the size of an X-ray irradiation region on which the beam of X-rays is irradiated through the object;
a shutter arranged around an X-ray irradiation axis for regulating the X-ray irradiation region depending on the size preset by the irradiation region setting unit; and
a laser pointer arranged on the shutter for visually indicating the X-ray irradiation region, the laser pointer being movable in synchronism with movement of the shutter.

9. The X-ray device as recited in claim 8, wherein the laser pointer comprises a laser irradiation unit configured to indicate the X-ray irradiation region with a laser identification mark.

10. The X-ray device as recited in claim 9, wherein the laser irradiation unit is fixedly arranged on an opposite surface of the shutter from the X-ray tube.

11. An X-ray device for irradiating a beam of X-rays on an object to capture an X-ray image of the object, comprising:
an X-ray tube for generating the beam of X-rays and irradiating the beam of X-rays on the object;
an irradiation region setting unit for presetting the size of an X-ray irradiation region on which the beam of X-rays is irradiated through the object;
a shutter arranged around an X-ray irradiation axis for regulating the X-ray irradiation region depending on the size preset by the irradiation region setting unit;
a laser pointer arranged independently of the shutter for visually indicating the X-ray irradiation region, the laser pointer being movable in synchronism with movement of the shutter; and
a drive unit associated with the irradiation region setting unit for driving the laser pointer in synchronism with movement of the shutter.

12. The X-ray device as recited in claim 11, wherein the laser pointer comprises a laser irradiation unit for indicating the X-ray irradiation region with a laser identification mark.

13. An X-ray device, comprising:
an X-ray generation unit configured to generate a beam of X-rays;
an image capturing unit for capturing an X-ray image;
a shutter configured to regulate an X-ray irradiation region on the image capturing unit; and
a laser pointer for visually indicating the circumference of the X-ray irradiation region on the image capturing unit, the laser pointer being movable in synchronism with movement of the shutter.

\* \* \* \* \*